United States Patent [19]

Curran et al.

[11] 4,046,895
[45] Sept. 6, 1977

[54] PHENANTHRIDINE DERIVATIVES AND RELATED COMPOUNDS

[75] Inventors: Adrian Charles Ward Curran, South Cave; Robin Gerald Shepherd, Burnham, both of England

[73] Assignee: John Wyeth & Brother Limited, Maidenhead, England

[21] Appl. No.: 651,748

[22] Filed: Jan. 23, 1976

[30] Foreign Application Priority Data

Feb. 5, 1975 United Kingdom ............... 4967/75

[51] Int. Cl.$^2$ .................... C07D 215/48; A61K 31/47
[52] U.S. Cl. ............... 424/258; 260/283 S; 260/283 CN; 260/286 A; 260/288 CF
[58] Field of Search ......... 260/283 S, 283 CF, 286 A; 424/258

[56] References Cited

U.S. PATENT DOCUMENTS 3,963,722  6/1976  Curran ........................... 260/283 S Primary Examiner—Donald G. Daus
Assistant Examiner—David E. Wheeler
Attorney, Agent, or Firm—Arthur E. Wilfond

[57] ABSTRACT

The invention provides a compound of formula I

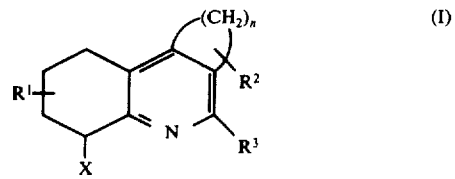

wherein $R^1$ and $R^2$ are the same or different and represent hydrogen or alkyl of 1-6 carbon atoms, $R^3$ represents hydrogen, alkyl of 1-6 carbon atoms, or phenyl, X is Na, K, Li, or CSNHR$^4$ wherein R$^4$ is hydrogen or alkyl of 1-6 carbon atoms and n is 3, 4 or 5 or a pharmaceutically acceptacle acid addition salt of a compound where X is CSNHR$^4$.

The compounds of formula I wherein X is CSNHR$^4$ are anti-ulcer agents. Those in which X is Na, K or Li are intermediates.

5 Claims, No Drawings

PHENANTHRIDINE DERIVATIVES AND RELATED COMPOUNDS

The invention relates to novel phenanthridine derivatives, and related compounds and to pharmaceutical compositions containing them.

The invention provides compounds of formula I

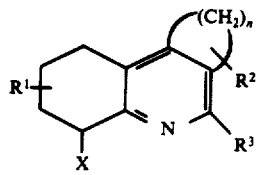

wherein $R^1$ and $R^2$ are the same or different and represent hydrogen or alkyl of 1-6 carbon atoms, $R^3$ represents hydrogen, alkyl of 1-6 carbon atoms or phenyl, X represents Na, K, Li or $CSNHR^4$ wherein $R^4$ is hydrogen or alkyl of 1-6 carbon atoms and $n$ is 3, 4 or 5 and pharmaceutically acceptable acid addition salts of compounds where X is $CSNHR^4$. The alkyl radical $R^1$, $R^2$, $R^3$ or $R^4$ may be a straight or branched chain, having from 1 to 6 carbon atoms, e.g. methyl, ethyl, $n$, and iso-propyl and n-, s- and t-butyl.

Particularly preferred compounds are those in which $R^1$ and $R^2$ are selected from methyl and hydrogen. Also preferred are compounds wherein $n$ is 4. Compounds wherein $R^3$ is hydrogen are also preferred. Preferably $R^4$ is hydrogen.

Thus the present invention provides, in one preferred aspect, compounds of formula II

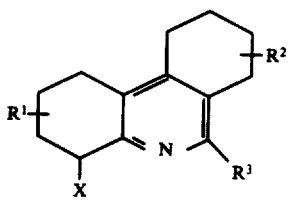

and pharmaceutically acceptable acid addition salts of those compounds where X is $CSNHR^4$, wherein $R^1$, $R^2$ and $R^3$ and X are as defined in connection with formula I. In formula II, it is preferred that X is $CSNH_2$.

A preferred compound of formula II is 1,2,3,4,7,8,9,10-octahydrophenanthridine-4-thiocarboxamide and the pharmaceutically acceptable acid addition salts thereof.

The compounds of formula I where X is $CSHR^4$ can form acid addition salts with inorganic acids e.g. hydrochloric, hydrobromic, sulphuric or nitric acids, or organic acids e.g. citric, fumaric, maleic or tartaric acids. These acid addition salts are included in the invention.

In the compounds of formula I the carbon atom to which X is attached is asymmetric. Consequently the compounds can exist in optically active $d$ and $l$ forms. These optically active forms and the racemates are included in the invention. The optically active forms may be separated by standard techniques either by formation of an acid salt with an optically active acid or by use of an optically active base with a precursor compound in which X is COOH.

Compounds of formula I, wherein X is $CSNHR^4$ are anti-ulcer agents. Activity is determined either by the stress-induced test of Senay and Levine, Proc.Soc.Ex-p.Biol.Med. 124, 1221-1223 (1967) or the antisecretory test of H. SHay, D. Sun and H. Greenstein, Gastroenterology 1954, 25, 906-13. In general compounds of formula I in which X is $CSNHR^4$ are active in one or both of these tests. Compounds of formula I in which X is Na, K or Li are intermediates for compounds of formula I, in which X is $CSNHR^4$.

The compounds of formula I may be prepared by various methods.

A general method of preparing the compounds of formula I comprises treating a corresponding compound in which X is hydrogen by known methods to introduce the desired group X. The most convenient intermediate compounds are those in which X is Na, K or Li since such compounds can be used to prepare the other compounds of formula I.

Compounds of formula I wherein X is Na, K or Li may be prepared by treating a corresponding compound of formula I wherein X is hydrogen, with a metal alkyl, or a metal amide. The metal alkyl may be a compound $MR^6$ wherein $M$ is sodium, potassium or lithium and $R^6$ is alkyl, aryl or aralkyl e.g. lower alkyl such as n-butyl or aryl e.g. phenyl.

The metal amide may be a compound MA wherein M is sodium, potassium or lithium and A is a secondary amine radical. The metal amide may be formed in situ by reacting a metal alkyl $MR^6$ as defined above with a secondary amine (preferably in a molar amount equal to that of the metal alkyl). The compound of formula I wherein X is hydrogen may then be added.

Preferably the metal M is lithium. The secondary amine may be a dialkylamine e.g. diethylamine, di-isopropylamine, di-tertiarylbutyl amine, di-n-decylamine, dicyclohexylamine, N-tertiaryamyl-N-t-butylamine, N-isopropyl-N-cyclohexylamine, or N(1'-ethylcyclohexyl)-1,1,3,3,tetramethylbutylamine or a cyclic compound e.g. piperidine, or 2,2,6,6-tetramethylpiperidine.

A general method for preparing thioamides of formula (I) wherein X is $CSNH_2$ comprises treating a compound of formula I wherein X is Na, K or Li with a silyl compound of formula $R_xSi(NCS)_{4-x}$ wherein R is an alkyl, aryl or aralkyl residue and $R_x$ may be any mixture of these, and $x$ has a value of from 0 to 3, then subjecting the product to hydrolysis or alcoholysis. The method may also be used to prepare nitriles of formula I wherein X is CN by employing a compound of formula $R_3SiNCS$ and a molar ratio of $R_3SiNCS$: Compound I where X is hydrogen of at least 2 : 1. Under these conditions a mixture of a compound of formula I where X is CN and where X is $CSNH_2$ may be formed. With a higher ratio e.g. 4 : 1 the nitrile may be formed exclusively.

Examples of the compound of formula $R_xSi(NCS)_{4-x}$ are:

$x = 0 : Si(NCS)_4$
$x = 1 : RSi(NCS)_3$
$x = 2 : R_2Si(NCS)_2$
$x = 3 : R_3SiNCS$ wherein R has any of the meanings given above.

When $x$ is 3 the residue $R_xSi$ may be a tri-alkyl-, triaryl- or tri-aralkyl-silyl group and is preferably a tri-lower alkyl silyl group, e.g. trimethylsilyl.

The reaction with the compound of formula $R_xSi(NCS)_{4-x}$ is conducted under anhydrous conditions, preferably in an inert solvent, for example a hydrocarbon solvent such as benzene, toluene or hexane. Ethers including cyclic ethers such as tetrahydrofuran should be avoided. Conveniently the starting material of formula I wherein X is Na, K or Li is prepared in situ and the same solvent is used for the reaction with the compound of formula $R_xSi(NCS)_{4-x}$.

The product of the first stage is a compound of formula III

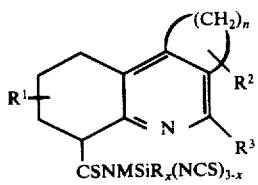

wherein $R^1$, $R^2$, $R^3$, and $n$, are as defined in connection with formula I, M is Na, K or Li and R and $x$ are as defined above. The compound of formula III is converted by water or alcohol to the desired compound of formula I, presumably via a transient intermediate of formula (IV)

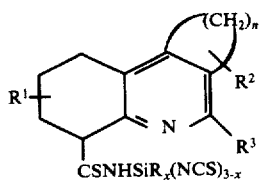

wherein R is the organic residue defined above, $x$ is as defined above, and $R^1$, $R^2$, $R^3$, and $n$ are as defined in connection with formula I.

Compounds of formula III and IV are included in the invention as is the process for preparing them described above. These compounds are not isolated but are obtained and used in solution.

The desired compound of formula I wherein X is $CSNH_2$ is conveniently formed by treating a compound of formula III with water or a lower alkanol e.g. ethanol.

When a compound of formula I in which $R^3$ is methyl is treated with a metal alkyl $MR^6$ as discussed previously the metal atom may be inserted either at the desired X position or in the methyl group $R^3$. This side reaction may also occur with any compound containing an alkyl group $R^3$ in which there are one or two hydrogen atoms on the carbon atom adjacent to the pyridine ring. These by-products which contain a metal atom in an alkyl group $R^3$ would not normally react with the compound $R_xSi(NCS)_{4-x}$.

Compounds of formula I wherein X is $CSNHR^4$ and $R^4$ is alkyl may be prepared by reacting a compound of formula I wherein X is M, M being Na, K, or Li, with a compound of formula $R^4NCS$ where $R^4$ is as defined above and treating the product with hydrogen ions.

Preferably a starting material of formula I wherein M is lithium is used. Conveniently the product after reaction with $R^4NCS$ is treated with acid, e.g. an aqueous mineral acid such as a hydrohalic acid preferably hydrochloric acid. Alternatively, any other proton source may be used e.g. water or an alcohol e.g. a lower alkanol such as methanol, or ethanol, or acetic acid.

The desired compound of formula I wherein X is $CSNHR^4$ may be accompanied by a bisthioamide of formula V;

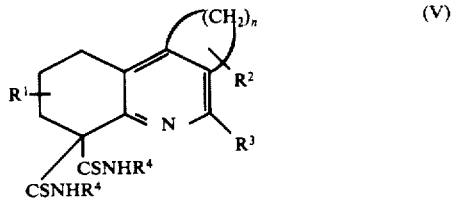

such bisthioamides may be removed by standard techniques e.g. fractional crystallisation.

Compounds of formula I in which X is $CO_2R^5$ and $R^5$ is hydrogen or alkyl of 1-6 carbon atoms are intermediates for the compounds of formula I, wherein X is $CSNHR^4$. The compounds of formula I wherein X is $CO_2R^5$ may be prepared by treatment of a compound of formula I wherein X is M and M is Na, K or Li with carbon dioxide. Usually the compound of formula I wherein X is M is prepared in situ by a method as previously described. This is followed by treatment of the product in situ with carbon dioxide, conveniently by bubbling $CO_2$ gas into the reaction mixture. The compound of formula I in which X is $CO_2H$ is obtained by treatment of the product, a metal salt of a compound of formula I in which X is COOH, with acid e.g. hydrochloric or hydrobromic acid. A convenient method is to treat a solution of the salt with gaseous hydrogen chloride.

If a compound of formula I in which $R^3$ is alkyl is used and the metal atom has been inserted on this alkyl group (as discussed above), the carboxylation may occur either on the alkyl group $R^3$ or at the desired X position. Usually a mixture of desired and undesired product is formed but the desired product can be separated at a later stage.

The esterification of a compound of formula I in which X is $CO_2H$ may be carried out using an hydroxyl compound $R^5OH$, wherein $R^5$ is alkyl of 1-6 carbon atoms according to standard procedures, e.g. in the presence of an acid catalyst e.g. some concentrated sulphuric acid or after saturation with hydrogen chloride gas, or a Lewis acid catalyst e.g. boron trifluoride if desired with heat or treatment of the silver salt (X is COOAg) with an iodide $R^5I$ wherein $R^5$ is alkyl of 1-6 carbon atoms.

The yield of ester may be improved by introducing a further quantity of the metal alkyl (used to prepare the starting material) after the $CO_2$ treatment, followed by a further amount of $CO_2$. This procedure gives the bis acid metal salt of formula VI

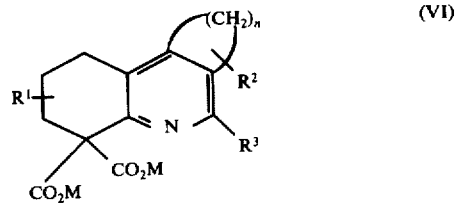

wherein $R^1$, $R^2$ and $R^3$ are as defined in connection with formula I and M is as defined above. This salt spontaneously decarboxylates during the esterification.

A further method for preparing esters of formula I wherein X is $CO_2R^5$ comprises treating a compound of formula I as defined above wherein X is M with a haloformate of formula $HalCOOR^5$ wherein Hal is a halogen atom e.g. chlorine or bromine and $R^5$ is alkyl of 1-6 carbon atoms. The product is usually a mixture of the desired compound of formula I wherein X is $CO_2R^5$ and the corresponding bis-ester corresponding to formula (VI), wherein M is replaced by $R^5$. These bis-esters may be used for preparing the corresponding compounds of formula I wherein X is $CO_2H$. This mixture of mono and bis esters may be converted directly to the corresponding compound of formula I where X is $CO_2H$, by saponification with an alkali or alkaline earth metal hydroxide to give a mixture of the metal salt of the mono acid of formula I wherein X is $CO_2H$ and the metal salt of the diacid of formula VI wherein M is H. Treatment of this mixture with a mineral acid e.g. hydrochloric acid gives the desired acid of formula I wherein X is $CO_2H$ since the diacid spontaneously decarboxylates to form the mono acid.

The product of the haloformate reaction may be treated with a further quantity of the metal alkyl (used to prepare the starting material) followed by a further quantity of the haloformate thereby producing more of the bis ester corresponding to formula (VI) wherein M is replaced by $R^5$.

A further method for preparing compounds of formula I in which X is $CO_2H$ comprises decarboxylation of a compound of formula VI wherein M is $R^5$. The decarboxylation can be carried out by heating the dicarboxylic acid of formula VI wherein M is hydrogen. Usually the dicarboxylic acid may be prepared in situ by hydrolysis of the corresponding di-ester, wherein $R^5$ is as defined above except hydrogen. The hydrolysis and decarboxylation may be carried out by heating with a dilute mineral acid e.g. HCl or sulphuric acid or the diester may be saponified with alkali e.g. sodium or potassium hydroxide. The resulting salt is then acidified and decarboxylated by heating.

Compounds of formula I, in which X is $CONHR^4$ are also intermediates and may be prepared by treatment of a corresponding compound of formula I wherein X is COCl or $CO_2R^5$ and $R^5$ is lower alkyl, with ammonia to give a compound of formula I in which X is $CONH_2$, which may be subsequently alkylated to introduce the group $R^4$ when alkyl. Conveniently, a compound of formula I wherein X is $CO_2R^5$ wherein $R^5$ is lower alkyl, especially methyl or ethyl, is treated with ammonia. Alternatively substituted amides of formula I wherein X is $CONHR^4$ and $R^4$ is alkyl may be prepared by treatment of the carboxylic ester of formula I wherein X is $CO_2R^5$ and $R^5$ is other than hydrogen with an amine of formula $R^4NH_2$ wherein $R^4$ is alkyl. The substituted amides may conveniently be prepared from the acid chloride of formula I wherein X is COCl by treatment with a primary amine $R^4NH_2$. An example of a primary amine which may be used in the above reactions is methylamine.

The acid chlorides may be prepared by treatment of the corresponding acid of formula I, wherein X is $CO_2H$ with thionyl chloride, phosphorus oxychloride or phosphorus pentachloride.

A further process for preparing intermediate compounds of formula I wherein X is $CONHR^4$ wherein $R^4$ is hydrogen or alkyl, comprises treating an ester compound of formula I, wherein X is $CO_2R^5$ and $R^5$ is alkyl with an amide of formula $R^8CONHR^4$ or a salt thereof wherein $R^4$ is hydrogen or alkyl and $R^8$ is hydrogen or lower alkyl in the presence of an alkali-metal alkoxide.

Preferably a molar equivalent of alkali-metal alkoxide is used for each mole of ester of formula I. The alkali-metal alkoxide may be one derived from a lower alkanol having from 1 to 6 carbon atoms e.g. methanol or ethanol. The alkali-metal is preferably sodium.

The ester of formula I is preferably a lower alkyl ester.

The amide $R^8CONHR^4$ is preferably one in which $R^8$ is hydrogen or methyl. $R^4$ is also preferably hydrogen or methyl. Thus preferred amides are formamide, N-methylformamide, acetamide and N-methylacetamide. Salts especially alkali-metal salts of these amides may be used as starting materials.

The reaction may be carried out by heating the reactants together.

The amides of formula I, wherein X is $CONH_2$ may also be prepared by partial hydrolysis of the corresponding nitriles of formula I, wherein X is CN. This hydrolysis may be accomplished in conventional manner e.g. by concentrated (e.g. 96%) sulphuric acid.

Thioamides of formula I wherein X is $CSNHR^4$ wherein $R^4$ is as already defined may be prepared by treatment of the corresponding compounds in which X is $CONHR^4$ with $P_2S_5$, e.g. by refluxing in pyridine. As mentioned below when the starting material is one in which X is $CONH_2$, decomposition to the nitrile may occur. This decomposition can be avoided by conducting the $P_2S_5$ reaction in the presence of $H_2S$. Alternatively the thioamides may be prepared by treatment of a nitrile of formula I, wherein X is CN with $H_2S$ to give the unsubstituted thioamide wherein X is $CSNH_2$. Substituted thioamides may be obtained by conducting this reaction in the presence of a primary amine $R^4NH_2$ wherein $R^4$ is alkyl. The $H_2S$ reaction can be carried out in a suitable solvent in the presence of a catalyst such as a tertiary amine e.g. a trialkylamine such as triethylamine.

Substituted thioamides may also be prepared by treatment of an unsubstituted thioamide of formula I, wherein X is $CSNH_2$ with an amine of formula $R^4NH_2$ where $R^4$ is alkyl in the presence of $H_2S$. The amine may be methylamine.

The nitriles of formula I wherein X is CN, may be prepared by dehydration of the corresponding amides of formula I wherein X is $CONH_2$. Such dehydration may be carried out with $P_2O_5$ as the dehydrating agent. Other dehydrating agents are phosphorus pentachloride or thionyl chloride. Decomposition to the nitrile may also occur as a side reaction during the conversion of the amides of formula I wherein X is $CONH_2$ to the corresponding thioamides wherein X is $CSNH_2$ using $P_2S_5$. The nitrile may either be separated, e.g. by chromatography or the mixture treated with $H_2S$ for conversion of the nitrile to the corresponding thioamide. The dehydration may also be effected by heating the amide in hexamethylphosphorictriamide as solvent. When using this solvent a compound of formula I in which X is $CONMe_2$ may be formed as a by-product. -product.

A further method for preparing the thioamides of formula I, wherein X is $CSNH_2$ comprises reacting a nitrile of formula I wherein X is CN with a thioamide of formula $R^9CSNH_2$ where $R^9$ is an alkyl group, e.g. a lower-alkyl group of 1–6 carbon atoms, preferably a methyl group, in a suitable solvent such as dimethylformamide saturated with hydrogen chloride.

The starting compounds of formula I wherein X is hydrogen are either known compounds or may be prepared by known methods.

A particularly preferred method for preparing a compound of formula I wherein X is hydrogen comprises hydrogenating a quinoline compound of formula VII

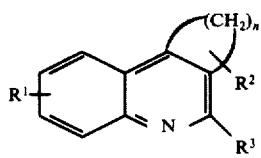
(VII)

wherein R¹, R² and R³ are as defined in connection with formula I in a strongly acidic medium in the presence of a platinum oxide catalyst. A preferred way of conducting this reaction is to employ a hydrogen halide salt of the compound of formula VII dissolved in acetic acid e.g. glacial acetic acid to which a small proportion (e.g. up to 20% but preferably not more than 5-10%) of water may be added to assist solution.

The invention also includes pharmaceutical compositions comprising an effective amount of a compound of formula I wherein X is CSNHR⁴ and R⁴ is as defined in connection with formula I, and a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxy-methyl cellulose, a low melting wax, and cocoa butter. The term "composition" is intended to include the formulation of an active ingredient with encapsulating material as carried to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxy-methyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be carried or adjusted from 25 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminum hydroxide, magnesium hydroxide or bismuth carbonate, aluminum glycinate, calcium carbonate magnesium trisilicate, sodium bicarbonate or the alumina gel described in British specification No. 1,284,394.

The invention is illustrated by the following Examples.

EXAMPLE 1

1,2,3,4,7,8,9,10-Octahydrophenanthridine 7,8,9,10-Tetrahydrophenanthridine hydrochloride (29 g, 0.13 mole) was dissolved in a mixture of glacial acetic acid (200 ml.) and water (10 ml.) and hydrogenated at 50 psi of hydrogen and room temperature over platinum oxide (750 mg.) until the theoretical uptake of hydrogen (0.26 mole) was observed. The solution was filtered and the solvents removed under reduced pressure. The residue was dissolved in water (100 ml.), and pH adjusted to 9 with $Na_2CO_3$ and the solution extracted with diethyl ether (3 × 100 ml.). Drying ($MgSO_4$) and evaporation of the combined organic layers gave a colourless oil, distillation of which gave the title compound (24.5 g, 99%) Bpt 110°-2° C/0.05 mm Found: C, 82.8; H, 9.3; N, 7.1%. Calc. for $C_{13}H_{17}N$: C, 83.4; H, 9.2; N, 7.5.

EXAMPLE 2

1,2,3,4,7,8,9,10-Octahydrophenanthridine-4-thiocarboxamide

A solution of 1,2,3,4,7,8,9,10-Octahydrophenanthridine (17.1 g, 0.91 mole) in benzene (100 ml.) was cooled to 0° C and treated portionwise under an invert atmosphere with a 9% w/v solution of n-butyl-lithium in hexane (40 ml. 0.56 mole). After the addition was complete the mixture was stirred for a further 0.5 h and the resulting 4-lithio-1,2,3,4,7,8,9,10-octahydrophenanthridine then treated in situ with trimethylsilylisothiocyanate (13 ml., 0.91 mole) and stirred a further hour. The reaction mixture was treated with 2N HCl (100 ml.), the layers separated and the aqueous layer washed with ethyl acetate (100 ml.). The pH of the aqueous solution was adjusted to 9 with $Na_2CO_3$ and the solution was extracted with chloroform (3 × 100 ml.). Drying ($MgSO_4$) and evaporation of the combined organic layers gave a yellow oil which crystallised in trituration with hexane. Recrystallisation of the solid from benzene gave the title compound as white needles (4 g, 18%) M.P. 162° C.

Found: C, 68.4; H, 7.4; N, 11.3. $C_{14}H_{18}N_2S$ requires C, 68.2; H, 7.4; N, 11.4%.

EXAMPLE 3

1,2,3,4,7,8,9,10-Octahydro-6-methylphenanthridine-4-thiocarboxamide

By the method of Example 2, 1,2,3,4,7,8,9,10-octahydro-6-methyl-phenanthridine is reacted with n-butyl-lithium solution and the resulting anion is reacted with trimethylsilyl isothiocyanate to give 1,2,3,4,7,8,9,10-octahydro-6-methylphenanthridine-4-thiocarboxamide.

EXAMPLE 4

1,2,3,4,7,8,9,10-Octahydro-6-phenylphenanthridine-4-thiocarboxamide

By the method of Example 2, 1,2,3,4,7,8,9,10-octahydro-6-phenyl-phenanthridine is reacted with n-butyl-lithium solution to give 1,2,3,4,7,8,9,10-octahydro-4-lithio-6-phenylphenanthridine which in turn is reacted with trimethylsilyl isothiocyanate to give 1,2,3,4,7,8,9,10-octahydro-6-phenylphenanthridine-4-thiocarboxamide.

EXAMPLE 5

1,2,3,4,7,8,9,10-Octahydro-2-methylphenanthridine-4-thiocarboxamide 7,8,9,10-Tetrahydro-2-methylphenanthridine is hydrogenated, by the method of Example 1, to give 1,2,3,4,7,8,9,10-octahydro-2-methylphenanthridine which is reacted with n-butyl-lithium solution followed by trimethylsilyl isothiocyanate using the procedure in Example 2 to give the title compound.

EXAMPLE 6

1,2,3,4,7,8,9,10-Octahydro-8-methylphenanthridine-4-thiocarboxamide 7,8,9,10-Tetrahydro-8-methylphenanthridine is hydrogenaated, by the method of Example 1, to give 1,2,3,4,7,8,9,10-octahydro-8-methylphenanthridine which is converted by the method of Example 2 into 1,2,3,4,7,8,9,10-octahydro-8-methylphenanthridine-4-thiocarboxamide.

EXAMPLE 7

6,7,8,9-Tetrahydro-3,4-cyclopentenoquinoline-6-thiocarboxamide 3,4-Cyclopentenoquinoline is hydrogenated, by the method of Example 1, to give 6,7,8,9-tetrahydro-3,4-cyclopentenoquinoline which is reacted with n-butyl-lithium solution followed by trimethylsilyl isothiocyanate according to the method of Example 2 to give 6,7,8,9-tetrahydro-3,4-cyclopentenoquinoline-6-thiocarboxamide.

EXAMPLE 8

1,2,3,4-Tetrahydro-3,4-cycloheptenoquinoline-4-thiocarboxamide 3,4-Cycloheptenoquinoline is hydrogenated, by the method of Example 1, to give 1,2,3,4-tetrahydro-3,4-cycloheptenoquinoline which is reacted with n-butyl-lithium solution followed by trimethylsilyl isothiocyanate, according to the method of Example 2, to give 1,2,3,4-tetrahydro-3,4-cycloheptenoquinoline-4-thiocarboxamide.

EXAMPLE 9

1,2,3,4,7,8,9,10-Octahydrophenanthridine-4-(N-methyl)thiocarboxamide 1,2,3,4,7,8,9,10-Octahydrophenanthridine-4-thiocarboxamide (1.25 g) was dissolved in ethanol (100 ml), previously saturated with hydrogen sulphide, and 33% ethanolic methylamine (50 ml). The mixture was heated in a bomb at 120° C for 3 days. Removal of the solvents gave a yellow oil. Column chromatography on silica using ethyl acetate as solvent gave the title compound as a quarterhydrate (150 mg. 11%) as pale yellow needles. m.p. 113° C.

Found: C, 68.3% H, 7.8% N, 10.5%, $C_{15}H_{20}N_2S.\frac{1}{4}$ $H_2O$ requires C, 68.0%; H, 7.8%; N, 10.5%.

Pharmacological test results 1,2,3,4,7,8,9,10-Octahydrophenanthridine-4-thiocarboxamide showed good activity in rats in the stress-induced test of Senay and Levine at 30 mg/kg but was inactive at 10 mg/kg. This compound also showed moderate activity in rats in the anti-secretory test of Shay et al. at 30 mg/kg.

We claim:

1. A compound of formula I

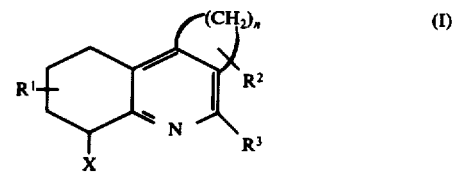

wherein $R^1$ and $R^2$ are the same or different and represent hydrogen or alkyl of 1–6 carbon atoms, $R^3$ represents hydrogen, alkyl of 1–6 carbon atoms, or phenyl, X is $CSNHR^4$ wherein $R^4$ is hydrogen or alkyl of 1–6 carbon atoms and n is 3, 4 or 5 or a pharmaceutically acceptable acid addition salt of a compound where X is $CSNHR^4$.

2. A compound as claimed in claim 1 which has the formula (II)

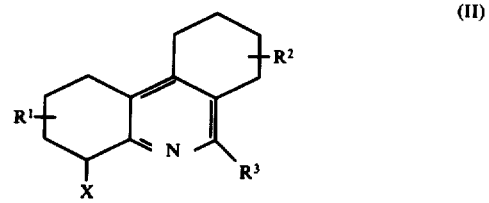

wherein $R^1, R^2$, $R^3$ and X are as defined in claim 1.

3. A compound as claimed in claim 1 which is 1, 2, 3, 4, 7, 8, 9, 10-Octahydrophenanthridine-4-thiocarboxamide or a pharmaceutically acceptable acid addition salt thereof.

4. An antiulcer composition comprising an effective amount of a compound of formula I as claimed in claim 1, wherein X is $CSNHR^4$ and a pharmaceutically acceptable carrier.

5. A pharmaceutical composition as claimed in claim 4, in unit oral dosage form.

* * * * *